(12) United States Patent
Hirokawa (10) Patent No.: US 12,423,784 B2
(45) Date of Patent: Sep. 23, 2025

(54) IMAGE PROCESSING METHOD, PROGRAM, OPHTHALMIC DEVICE, AND CHOROIDAL BLOOD VESSEL IMAGE GENERATION METHOD

(71) Applicant: NIKON CORPORATION, Tokyo (JP)

(72) Inventor: Mariko Hirokawa, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 37 days.

(21) Appl. No.: 18/582,890

(22) Filed: Feb. 21, 2024

(65) Prior Publication Data

US 2024/0188814 A1    Jun. 13, 2024

Related U.S. Application Data

(63) Continuation of application No. 17/025,575, filed on Sep. 18, 2020, now Pat. No. 11,941,788, which is a (Continued)

(30) Foreign Application Priority Data

Mar. 20, 2018    (JP) .................................. 2018-052246

(51) Int. Cl.
*G06T 7/62*     (2017.01)
*A61B 3/00*     (2006.01)
(Continued)

(52) U.S. Cl.
CPC .............. *G06T 5/77* (2024.01); *A61B 3/0025* (2013.01); *A61B 3/0058* (2013.01); *A61B 3/12* (2013.01);
(Continued)

(58) Field of Classification Search
CPC ......... G06T 5/005; G06T 7/0012; G06T 7/70; G06T 2207/10024; G06T 2207/30041;
(Continued)

(56) References Cited

U.S. PATENT DOCUMENTS 5,620,000 A    4/1997   Zinser et al.
8,205,991 B2   6/2012   Wei et al.
(Continued)

FOREIGN PATENT DOCUMENTS

GB    2 378 600 A    12/2003
JP    H07-146305 A    6/1995
(Continued)

OTHER PUBLICATIONS

Office Action issued in corresponding Chinese Patent Application No. 201980020423.0 dated May 31, 2023 (17 pages).
(Continued)

*Primary Examiner* — Chuong A Ngo
(74) *Attorney, Agent, or Firm* — Foley & Lardner LLP (57) ABSTRACT

An image processing method comprising acquiring a first fundus image obtained by photographing a fundus using first light having a first wavelength, and a second fundus image obtained by photographing the fundus using second light having a second wavelength that is shorter than the first wavelength; specifying, in the first fundus image, respective positions of retinal blood vessels appearing in the second fundus image; and generating a choroidal blood vessel image by processing the positions identified in the first fundus image.

14 Claims, 9 Drawing Sheets

Related U.S. Application Data continuation of application No. PCT/JP2019/011590, filed on Mar. 19, 2019.

(51) Int. Cl.
  *A61B 3/12* (2006.01)
  *A61B 3/14* (2006.01)
  *G06T 5/77* (2024.01)
  *G06T 7/00* (2017.01)
  *G06T 7/70* (2017.01)

(52) U.S. Cl.
  CPC .............. *A61B 3/14* (2013.01); *G06T 7/0012* (2013.01); *G06T 7/62* (2017.01); *G06T 7/70* (2017.01); *G06T 2207/10024* (2013.01); *G06T 2207/10048* (2013.01); *G06T 2207/10152* (2013.01); *G06T 2207/30041* (2013.01); *G06T 2207/30101* (2013.01)

(58) Field of Classification Search
  CPC ... G06T 2207/30101; G06T 5/77; G06T 7/62; G06T 2207/10048; G06T 2207/10152; A61B 3/12; A61B 3/14; A61B 3/0025; A61B 3/0058; A61B 3/16; G16H 15/00; G16H 30/40; G16H 30/20
  See application file for complete search history.

(56) References Cited

U.S. PATENT DOCUMENTS

| | | | |
|---|---|---|---|
| 2008/0007691 A1* | 1/2008 | Mihashi | G06T 7/33 351/206 |
| 2008/0007692 A1 | 1/2008 | Mihashi et al. | |
| 2016/0135683 A1 | 5/2016 | Yasuno et al. | |
| 2017/0112372 A1* | 4/2017 | Chakravorty | G06T 7/0012 |

FOREIGN PATENT DOCUMENTS

| | | |
|---|---|---|
| JP | 5739323 B2 | 6/2015 |
| JP | 2018-504234 A | 2/2018 |
| WO | WO-2016/124667 A2 | 8/2016 |

OTHER PUBLICATIONS

Office Action issued in corresponding Japanese Patent Application No. 2020-507857 dated May 16, 2023 (6 pages).

U.S. Non-Final Office Action on U.S. Appl. No. 17/025,575 dated Sep. 19, 2023 (12 pages).

U.S. Notice of Allowance on U.S. Appl. No. 17/025,575 dated Nov. 22, 2023 (9 pages).

\* cited by examiner

IMAGE PROCESSING METHOD, PROGRAM, OPHTHALMIC DEVICE, AND CHOROIDAL BLOOD VESSEL IMAGE GENERATION METHOD

CROSS-REFERENCE TO RELATED APPLICATIONS

This application is a continuation of U.S. application Ser. No. 17/025,575, filed on Sep. 18, 2020, which is a continuation of International Application No. PCT/JP2019/011590, filed on Mar. 19, 2019, which claims the benefit of and priority to Japanese Patent Application No. 2018-052246, filed Mar. 20, 2018, each of the foregoing are incorporated by reference herein in their entireties.

TECHNICAL FIELD

The present disclosure relates to an image processing method, a program, an ophthalmic device, and a choroidal blood vessel image generation method.

RELATED ART

Enhancing the characteristics of retinal blood vessels is disclosed in Japanese Patent No. 5739323.

SUMMARY

An image processing method of a first aspect of the technology of the present disclosure includes generating a choroidal blood vessel image based on a first fundus image obtained by photographing a fundus using first light having a first wavelength, and on a second fundus image obtained by photographing the fundus using second light having a second wavelength that is shorter than the first wavelength.

A program of a second aspect of the technology of the present disclosure causes a computer to execute the image processing method of the first aspect.

An ophthalmic device of a third aspect of the technology of the present disclosure is provided with a storage device in which is stored a program that causes a processor to execute an image processing method, and a processing device that executes the image processing method by executing the program stored in the storage device, wherein the image processing method is the image processing method of the first aspect.

A choroidal blood vessel image generation method of a fourth aspect of the technology of the present disclosure includes a step in which a fundus image is acquired by photographing a fundus using light having a wavelength of 630 nm or more, a step in which retinal blood vessels are extracted from the fundus image, and a step in which a choroidal blood vessel image is generated by deleting the retinal blood vessels from the fundus image.

DETAILED DESCRIPTION

Hereinafter, exemplary embodiments of the present invention will be described in detail with reference to the drawings. Note that, in the following, in order to facilitate the description, a scanning laser ophthalmoscope is abbreviated to an 'SLO'.

Figure 1:
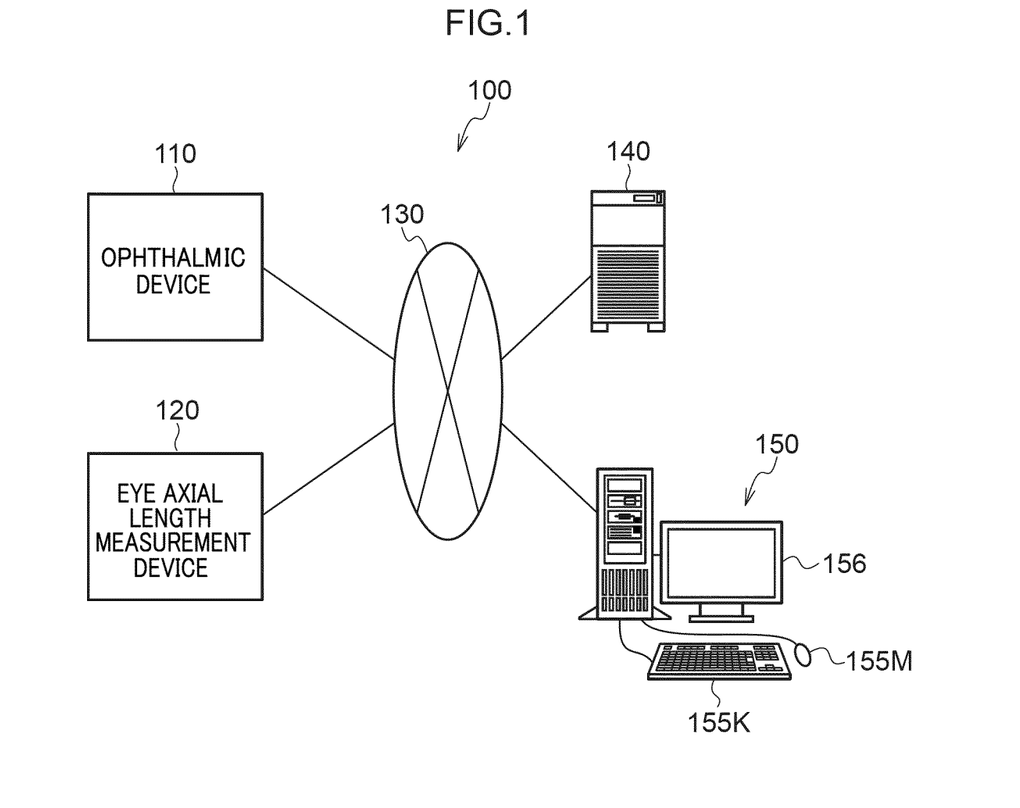
FIG. 1 is a block diagram of an ophthalmic system 100.

A structure of an ophthalmic system 100 will be described with reference to FIG. 1. As is shown in FIG. 1, the ophthalmic system 100 is provided with an ophthalmic device 110, an eye axial length measurement device 120, a management server device (hereinafter, referred to as a 'management server') 140, and an image display device (hereinafter, referred to as an 'image viewer') 150. The ophthalmic device 110 acquires fundus images. The eye axial length measurement device 120 measures an eye axial length of a patient. The management server 140 stores a plurality of fundus images and eye axial lengths that are obtained by photographing the fundus of a plurality of patients using the ophthalmic device 100. The stored fundus images and eye axial lengths are matched with an ID of the corresponding patient. The image viewer 150 displays fundus images acquired by the management server 140.

The ophthalmic device 110, eye axial length measurement device 120, management server 140, and image viewer 150 are mutually connected to each other via a network 130.

Note that it is also possible for other ophthalmic devices (i.e., examination instruments for perimetric measurement and tonometric measurement) and diagnostic supporting devices that perform image analysis using artificial intelligence to also be connected via the network 130 to the ophthalmic device 110, the eye axial length measurement device 120, the management server 140, and the image viewer 150.

Figure 2:
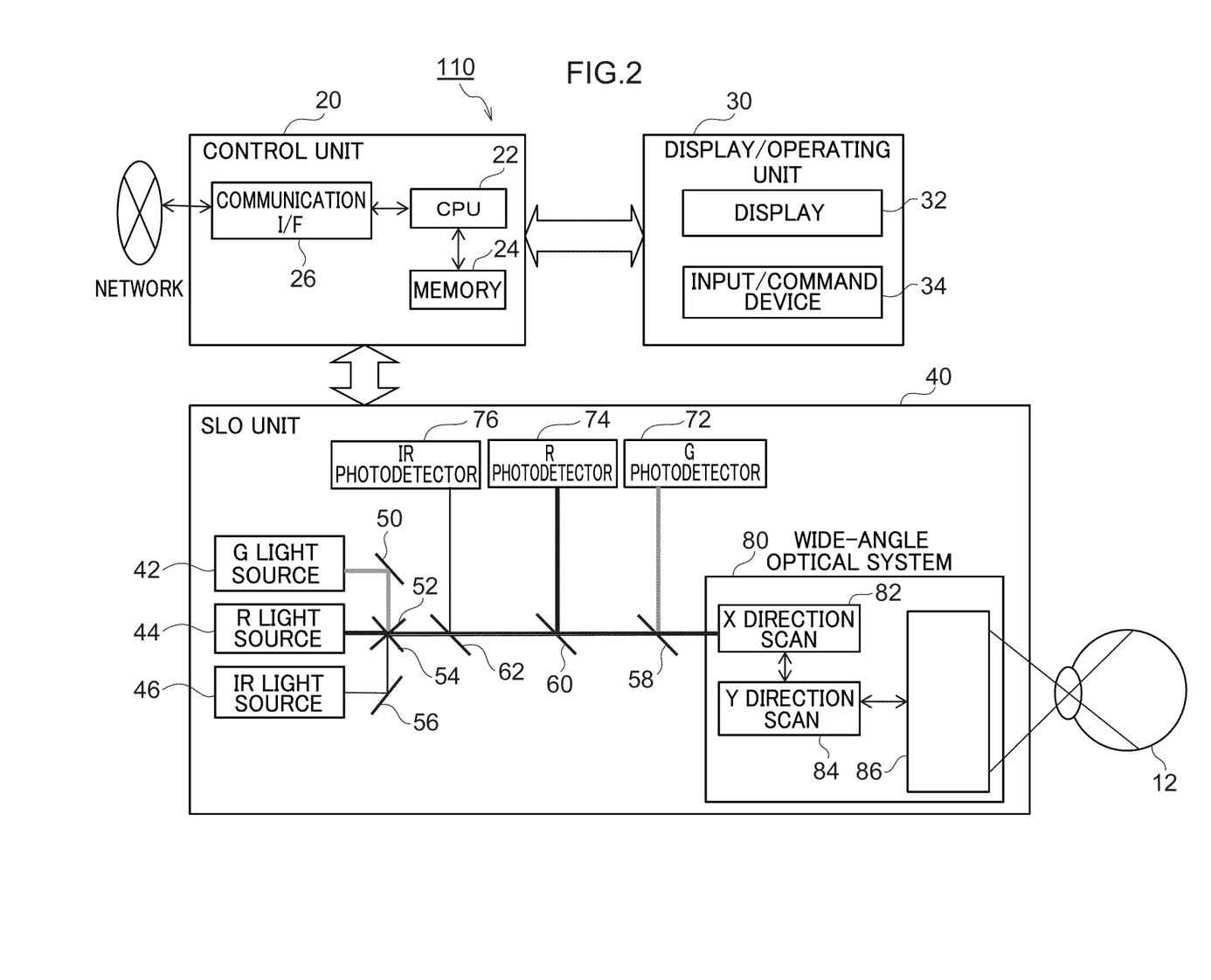
FIG. 2 is a schematic structural view showing an overall structure of an ophthalmic device 110.

Next, the structure of the ophthalmic device 110 will be described with reference to FIG. 2. As is shown in FIG. 2, the ophthalmic device 110 is provided with a control unit 20, a display/operating unit 30, and an SLO unit 40, and photographs a posterior segment (i.e., a fundus) of an eye that is being examined.

The control unit 20 is provided with a CPU 22, memory 24, and a communication interface (I/F) 26 and the like. The display/operating unit 30 is a graphic user interface that displays images obtained through photography and receives various commands including a command to take a photograph, and is provided with a display 32 and a touch panel 34.

The SLO unit 40 is provided with a light source 42 for G light (i.e., green light: having a wavelength of 530 nm), a light source 44 for R light (i.e., red light: having a wavelength of 650 nm), and a light source 46 for IR light (i.e., infrared light (near infrared light): having a wavelength of 800 nm). The light sources 42, 44, and 46 emit their respective types of light upon receiving a command from the control unit 20. The light source for the R light is a laser light source that emits visible light having a wavelength of 630~780 nm, while the light source for the IR light is a laser light source that emits near infrared light having a wavelength of 780 nm or more.

The SLO unit 40 is provided with optical systems 50, 52, 54 and 56 that reflect or transmit the light from the light sources 42, 44, and 46 so as to guide the light to a single optical path. The optical systems 50 and 56 are mirrors, while the optical systems 52 and 54 are beam splitters. The G light is reflected by the optical systems 50 and 54, the R light is transmitted through the optical systems 52 and 54, and the IR light is reflected by the optical systems 52 and 56, and each of these types of light is guided to the same optical path.

The SLO unit 40 is also provided with a wide-angle optical system 80 that scans the light from the light sources 42, 44, and 46 two-dimensionally across the posterior portion (i.e., the fundus) of the eye being examined 12. The SLO unit 40 is provided with a beam splitter 58 that reflects the G light out of the light from the posterior portion (i.e., the fundus) of the eye being examined 12, and transmits light other than the G light. The SLO unit 40 is also provided with a beam splitter 60 that reflects the R light out of the light transmitted through the beam splitter 58, and transmits light other than the R light. In addition, the SLO unit 40 is provided with a beam splitter 62 that reflects the IR light out of the light transmitted through the beam splitter 60. The SLO unit 40 is also provided with a G photodetector 72 that detects the G light reflected by the beam splitter 58, an R photodetector 74 that detects the R light reflected by the beam splitter 60, and an IR photodetector 76 that detects the IR light reflected by the beam splitter 62.

The wide-angle optical system 80 is provided with an X-direction scanning device 82 that is formed by a polygon mirror that scans the light from the light sources 42, 44, and 46 in an X direction, a Y-direction scanning device 84 that is formed by a galvanic mirror that scans this light in a Y direction, and an optical system 86 that includes a slit mirror and an elliptical mirror (not shown in the drawings) and widens the angle of the scanned light. The field of view (FOV) of the fundus is set to a wider angle by the optical system 86 than is achievable via the conventional technology, and it is possible to photograph a wider range of the fundus region than is achievable via the conventional technology. More specifically, as an external light irradiation angle from the outside of the eye being examined 12, it is possible to photograph a wide range of approximately 120 degrees of the fundus region (i.e., approximately 200 degrees as an internal light irradiation angle that is essentially capable of being photographed as a result of the fundus of the eye being examined 12 being irradiated with scanning light, when a center O of the eyeball of the eye being examined 12 is taken as a reference position). The optical system 86 may also be formed using a plurality of lens groups instead of using the slit mirror and elliptical mirror. In addition, two-dimensional scanners formed using MEMS mirrors may also be used for the respective scanning devices used for the X-direction scanning device 82 and the Y-direction scanning device 84.

When a system that includes a slit mirror and an elliptical mirror is used as the optical system 86, then it is possible to employ a structure in which a system that utilizes an elliptical mirror described in International Patent Application No. PCT/JP2014/084619 and in International Patent Application No. PCT/JP2014/084630 is used. The disclosures of International Patent Application No. PCT/JP2014/084619 (International Patent No. WO 2016/103484) filed internationally on Dec. 26, 2014, and of International Patent Application No. PCT/JP2014/084630 (International Patent No. WO 2016/103489) filed internationally on Dec. 26, 2014 are incorporated by reference in their entireties into the present application.

Note that the 'X direction' refers to a horizontal direction when the ophthalmic device 110 is placed on a horizontal surface, the 'Y direction' refers to a direction that is perpendicular to this horizontal surface, and a 'Z direction' refers to a direction that connects the center of the eyeball and the center of the pupil of an anterior segment of the eye being examined 12. Accordingly, the X direction, the Y direction, and the Z direction are mutually perpendicular to each other.

A color image of the fundus is obtained by photographing the fundus of the eye being examined 12 simultaneously using G light and R light. More specifically, the control unit 20 controls the light sources 42 and 44 such that they emit light simultaneously, and the G light and R light are scanned by the wide-angle optical system 80 across the fundus of the eye being examined 12. The G light reflected from the fundus of the eye being examined 12 is then detected by the G photodetector 72, and image data of a second fundus image (i.e., a G fundus image) is generated by an image processing unit 182. In the same way, the R light reflected from the fundus of the eye being examined 12 is detected by the R photodetector 74, and image data of a first fundus image (i.e., an R fundus image) is generated by the CPU 22 of the ophthalmic device 110. In addition, when IR light is reflected, the IR light reflected from the fundus of the eye being examined 12 is detected by the IR photodetector 76, and image data of an IR fundus image is generated by the CPU 22 of the ophthalmic device 110.

The CPU 22 of the ophthalmic device 110 mixes the first fundus image (i.e., the R fundus image) and the second fundus image (i.e., the G fundus image) together at a predetermined ratio, and displays the result as a color fundus image on the display 32. Note that instead of a color fundus image, it is also possible for the first fundus image (i.e., the R fundus image), the second fundus image (i.e., the G fundus image), or the IR fundus image to be displayed.

The image data of the first fundus image (i.e., the R fundus image), the image data of the second fundus image (i.e., the G fundus image), and the image data of the IR fundus image are sent from the ophthalmic device 110 to the management server 140 via the communication I/F 26.

Because the fundus of the eye being examined 12 is photographed using G light and R light simultaneously in this way, each positions of the first fundus image (i.e., the R fundus image) and the second fundus image (i.e., the G fundus image) correspond each other and are the same position on the fundus.

The eye axial length measurement device 120 shown in FIG. 1 has two modes, namely, a first mode and a second mode that are used to measure the eye axial length, which is the length in the eye axial direction (i.e., the Z direction) of the eye being examined 12. In the first mode, light from a light source (not shown in the drawings) is guided onto the eye being examined 12. Next, interference light generated by reflection light from the fundus and reflection light from the cornea is then received, and the eye axial length is measured based on an interference signal showing the received interference light. In the second mode, the eye axial length is measured using ultrasonic waves (not shown in the drawings). The eye axial length measurement device 120 transmits the eye axial length measured using either the first mode or the second mode to the management server 140. It is also possible for the eye axial length to be measured using both the first mode and the second mode and, in this case, an average of the eye axial lengths measured using both modes is transmitted to the management server 140 as being the eye axial length. The eye axial length is saved as one of patient data in the patient information held in the management server 140, and is also used for analyzing fundus images.

Figure 3:
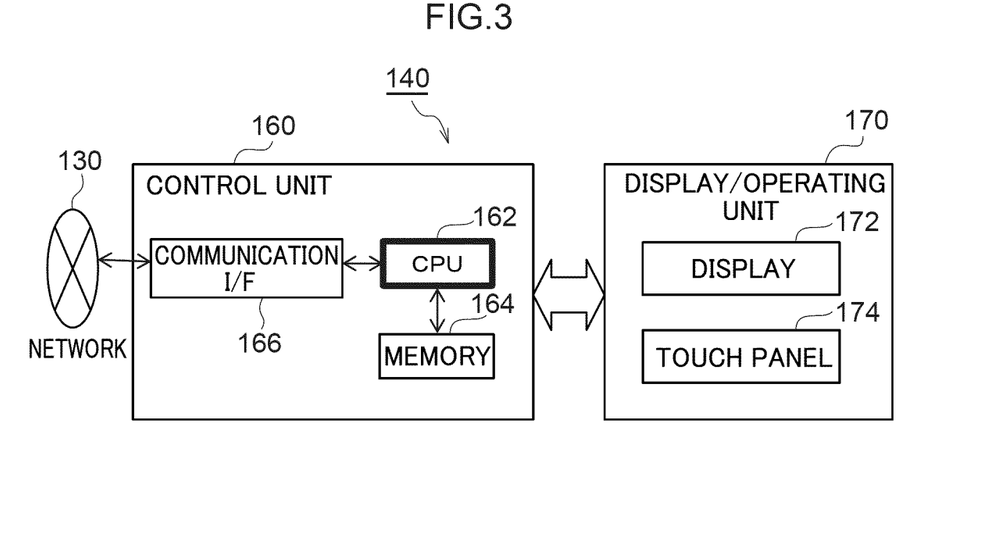
FIG. 3 is a block diagram showing a structure of an electrical system of a management server 140.

Next, a structure of the management server 140 will be described using FIG. 3. As is shown in FIG. 3, the management server 140 is provided with a control unit 160 and a display/operating unit 170. The control unit 160 is provided with a computer which includes a CPU 162, memory 164 which serves as a storage device, and a communication interface (I/F) 166 and the like. An image processing program is stored in the memory 164. The display/operating unit 170 is a graphic user interface that displays images, and receives various commands, and is provided with a display 172 and a touch panel 174.

The structure of the image viewer 150 is the same as that of the management server 140 and, therefore, no description thereof is given.

Figure 4:
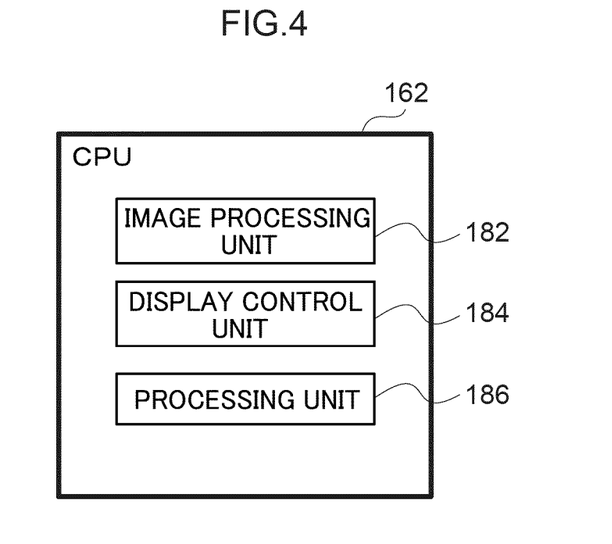
FIG. 4 is a block diagram showing functions of a CPU 162 of the management server 140.

Next, each of the various functions that are performed as a result of the CPU 162 of the management server 140 executing an image processing program will be described with reference to FIG. 4. The image processing program is provided with an image processing function, a display control function, and a processing function. As a result of the CPU 162 executing the image processing program having each of these functions, as is shown in FIG. 4, the CPU 162 is able to function as the image processing unit 182, a display control unit 184, and a processing unit 186.

Next, the image processing performed by the management server 140 will be described in detail using FIG. 5. As a result of the CPU 162 of the management server 140 executing the image processing program, the image processing shown in the flowchart in FIG. 5 is performed.

The image processing program is started when image data of a fundus image, which is obtained by photographing the fundus of the eye being examined 12 by the ophthalmic device 110, is transmitted from the ophthalmic device 110, and is received by the management server 140.

Figure 5:
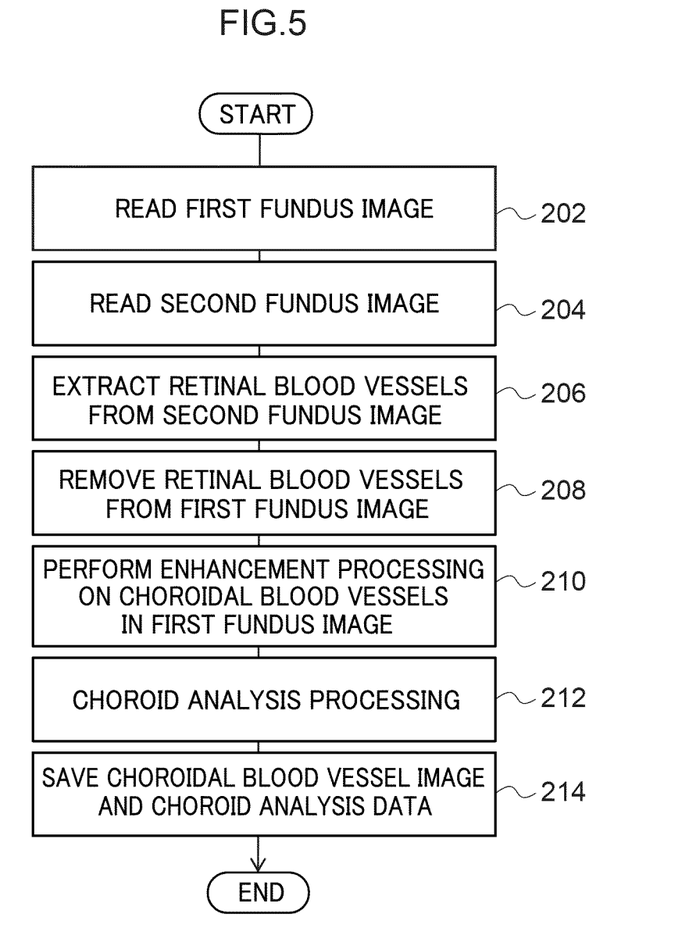
FIG. 5 is a flowchart for an image processing program.

Once the image processing program is started, in step 202 shown in FIG. 5, the processing unit 186 reads the image data of the first fundus image (i.e., the R fundus image) from the image data of a fundus image received from the ophthalmic device 110. In step 204, the processing unit 186 reads the image data of the second fundus image (i.e., the G fundus image) from the image data of a fundus image received from the ophthalmic device 110.

Figure 6A:
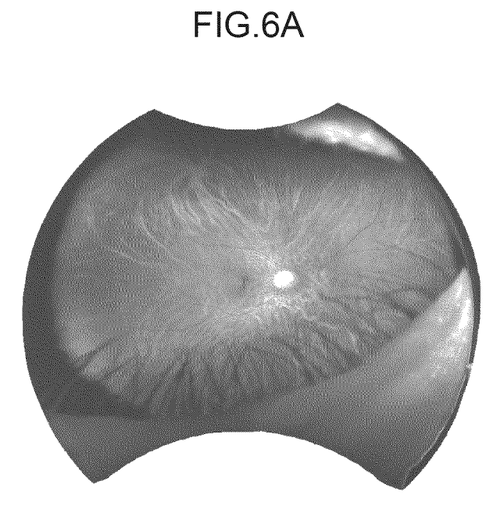
FIG. 6A is a view showing a first fundus image (i.e., an R (red color) fundus image).
Figure 6B:
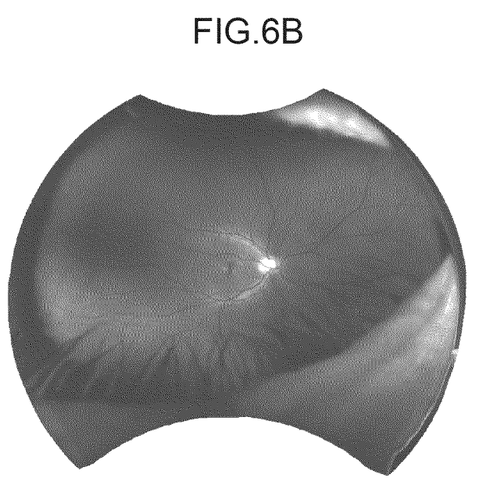
FIG. 6B is a view showing a second fundus image (i.e., a G (green color) fundus image).

Here, the information contained in the first fundus image (i.e., the R fundus image) and the second fundus image (i.e., the G fundus image) will be described.

The structure of an eye is such that a plurality of layers having mutually different structures cover a vitreous humor. Included among the plurality of layers are the retina, the choroid, and the sclera going from the innermost side on the vitreous humor side towards the outer side. R light passes through the retina and reaches the choroid. Accordingly, information about blood vessels present in the retina (i.e., retinal blood vessels) and information about blood vessels present in the choroid (i.e., choroidal blood vessels) are contained in the first fundus image (i.e., the R fundus image). In contrast to this, G light only reaches as far as the retina. Consequently, only information about blood vessels present in the retina (i.e., retinal blood vessels) is contained in the second fundus image (i.e., the G fundus image).

In step 206, as a result of the image processing unit 182 performing black-hat filtering on the second fundus image (i.e., the G fundus image), the retinal blood vessels are extracted from the second fundus image (i.e., the G fundus image). Black-hat filtering is filtering processing to extract black lines.

Black-hat filtering is processing to determine a difference between image data of the second fundus image (i.e., the G fundus image), and image data obtained by performing closing processing in which expansion processing and contraction processing are each performed N number of times (wherein N is an integer equal to or greater than 1) on this original image data. Because the retinal blood vessels absorb irradiated light (i.e., not only G light, but R light or IR light as well), in the fundus image they are photographed as appearing blacker compared to peripheral areas around the blood vessels. Because of this, the retinal blood vessels can be extracted by performing black-hat filtering on the fundus image.

In step 208, the image processing unit 182 removes the retinal blood vessels extracted in step 206 from the first fundus image (i.e., the R fundus image) by performing inpainting. More specifically, the retinal blood vessels are made to appear less prominent in the first fundus image (i.e., the R fundus image). Even more specifically, the respective positions of the retinal blood vessels extracted from the second fundus image (i.e., the G fundus image) are specified in the first fundus image (i.e., the R fundus image), and the pixel values of the pixels in the first fundus image (i.e., the R fundus image) at the specified positions are then processed so that the difference between these pixel values and the average value of the peripheral pixels surrounding these pixels falls within a predetermined range (for example, zero).

Figure 6C:
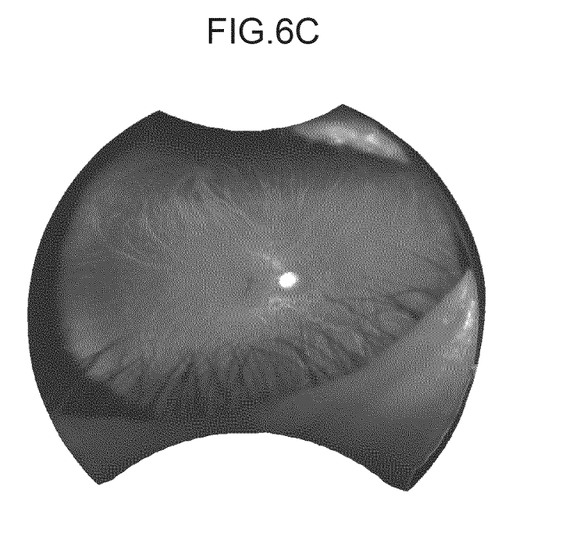
FIG. 6C is a view showing a choroidal blood vessel image in which choroidal blood vessels appear more prominent relatively.

In this way, because the retinal blood vessels are made to appear less prominent in the first fundus image (i.e., the R fundus image) in which both retinal blood vessels and choroidal blood vessels are present, the result is that the choroidal blood vessels can be made to appear more prominent relatively in the first fundus image (i.e., in the R fundus image). As a consequence, as is shown in FIG. 6C, a choroidal blood vessel image is obtained in which the choroidal blood vessels appear more prominent relatively.

Figure 6D:
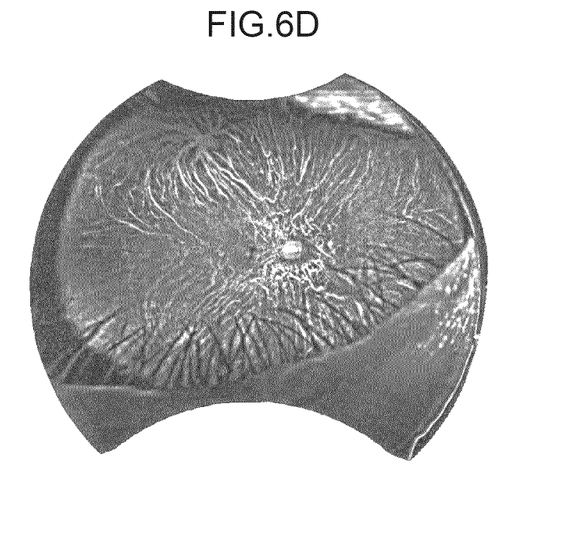
FIG. 6D is a view showing a choroidal blood vessel image in which the choroidal blood vessels have been enhanced.

In step 210, the image processing unit 182 enhances the choroidal blood vessels in the first fundus image (i.e., the R fundus image) by performing CLAHE (Contrast Limited Adaptive Histogram Equalization) processing on the image data of the first fundus image (i.e., the R fundus image) in which the choroidal blood vessels appear more prominent relatively. As a result, as is shown in FIG. 6D, a choroidal blood vessel image in which the choroidal blood vessels appear enhanced is obtained.

In step 212, the image processing unit 182 executes choroid analysis processing using the image data of the choroid blood vessel image in which the choroidal blood vessels have been enhanced. This choroid analysis processing may be, for example, vortex vein position detection processing or processing to analyze the orientation of the running direction of the choroidal blood vessels or the like.

In step 214, the processing unit 186 saves the choroidal blood vessel images and the choroid analysis data in the memory 164.

Once the processing of step 214 has ended, the image processing program also ends.

It should be noted that there may be cases in which the medical practitioner who is operating the image viewer 150 wishes to ascertain the state of the choroidal blood vessels when diagnosing a patient. In such cases, the medical practitioner transmits a command via the image viewer 150 to the management server 140 to transmit the data for a display screen for choroidal blood vessel analysis mode.

The display control unit 184 of the management server 140 that receives this command from the image viewer 150 then generates the data for a display screen for choroidal blood vessel analysis mode.

This data for a display screen for choroidal blood vessel analysis mode will now be described. When the fundus of a patient is being photographed, individual information pertaining to that patient is input into the ophthalmic device 110. This individual information includes the patient's ID, name, age, eyesight and the like. When the fundus of the patient is photographed, information showing whether the eye whose fundus is photographed is the right eye or the left eye is also input. In addition, when the fundus of a patient is photographed, the date and time of the photograph are also input. In addition to the image data of the fundus image, the individual information, the information showing which eye, and the data showing the date and time of the photograph are also transmitted from the ophthalmic device 110 to the management server 140.

Figure 7:
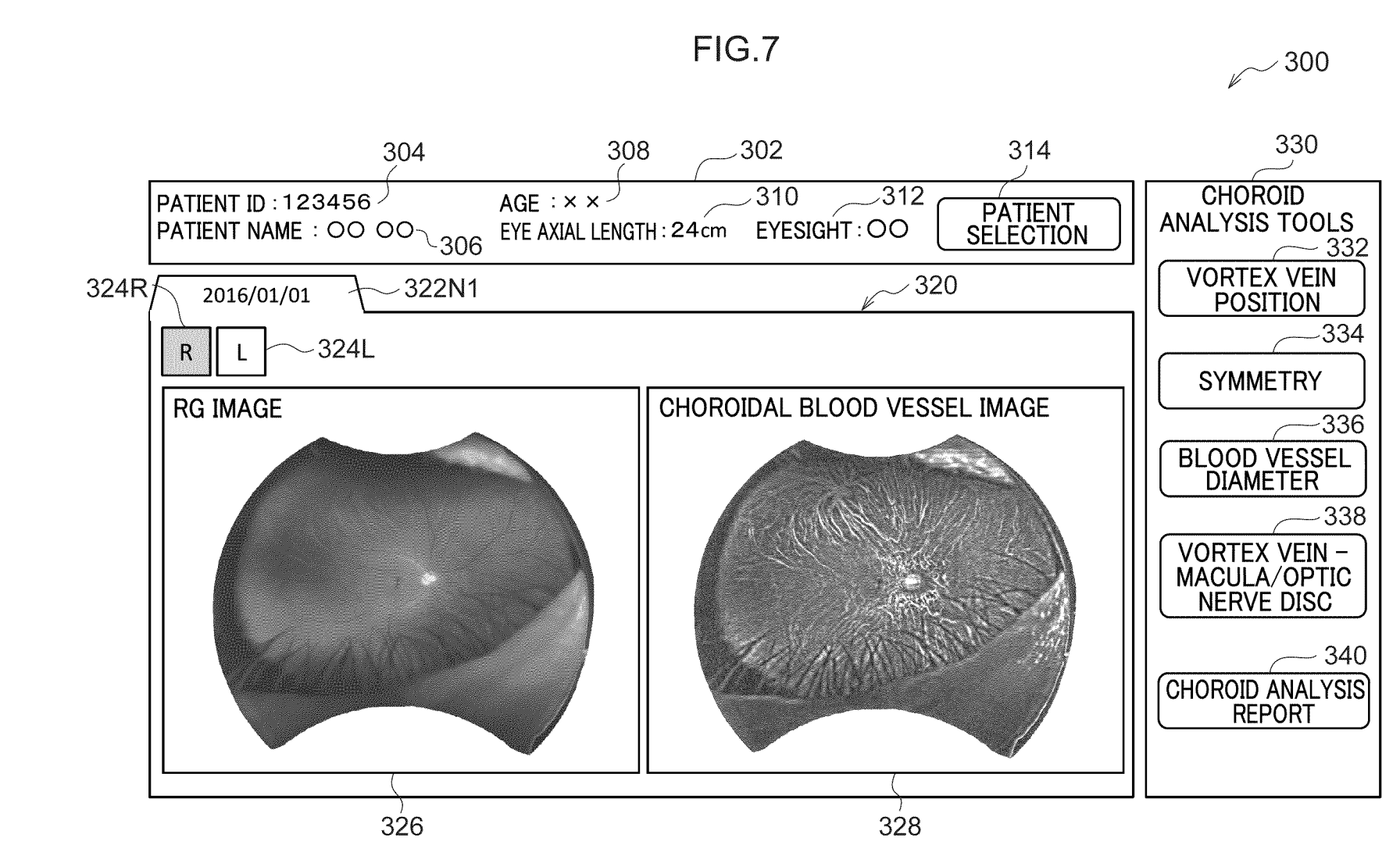
FIG. 7 is a view showing a display screen 300 of a choroidal blood vessel analysis mode when a fundus of a patient is initially photographed.

The display control unit 184 reads, as the data for a display screen for choroidal blood vessel analysis mode, the respective data items for the individual information including the patient's eye axial length, the date and time of the photograph, the information showing which eye, the first fundus image (i.e., the R fundus image), the second fundus image (i.e., the G fundus image), and the choroidal blood vessel image from the memory 164, and generates a display screen 300 for choroidal blood vessel analysis mode which is shown in

FIG. 7.

The management server 140 that has generated the display screen 300 transmits the data for the display screen 300 for choroidal blood vessel analysis mode to the image viewer 150. When the image viewer 150 receives this data for the display screen for choroidal blood vessel analysis mode, it displays FIG. 7 on the display 156 of the image viewer 150 based on the data for the display screen for choroidal blood vessel analysis mode.

Here, the display screen 300 for choroidal blood vessel analysis mode shown in FIG. 7 will be described. As is shown in FIG. 7, the display screen 300 for choroidal blood vessel analysis mode shown in FIG. 7 has an individual information display column 302 that displays individual information pertaining to the patient, an image display column 320, and a choroid analysis tool display column 330.

The individual information display column 302 has a patient ID display column 304, a patient name display column 306, an age display column 308, an eye axial length display column 310, and an eyesight display column 312.

The image display column 320 has a photograph date display column 322N1, a right eye information display column 324R, a left eye information display column 324L, and RG image display column 326, and a choroidal blood vessel image display column 328. Note that the RG image is an image which is obtained by synthesizing the first fundus image (i.e., the R fundus image) and the second fundus image (i.e., the G fundus image) with the size of each pixel value set at a predetermined ratio (for example, 1:1).

The choroid analysis tool display column 330 is provided with a plurality of choroid analysis tools that command the image viewer 150 to perform various types of processing such as, for example, a vortex vein position analysis icon 332, a symmetry icon 334, a blood vessel diameter icon 336, a vortex vein—macula/optic nerve disc icon 338, and a choroid analysis report icon 340. By selecting the vortex vein position analysis icon 332, it is commanded that the vortex vein position to be identified. By selecting the symmetry icon 334, it is commanded that the symmetry of the vortex vein to be analyzed. By selecting the blood vessel diameter icon 336, it is commanded that a tool that analyzes the diameter of the choroidal blood vessel to be employed. By selecting the vortex vein—macula/optic nerve disc icon 338, it is commanded that the relative positions between the vortex vein, the macula, and the optic nerve disc to be analyzed. By selecting the choroid analysis report icon 340, it is commanded that a choroid analysis report to be displayed.

In the example shown in FIG. 7, an RG image and a choroid blood vessel image of the fundus of a patient identified by the patient ID number 123456 that was photographed on Jan. 1, 2016 are displayed.

Figure 8:
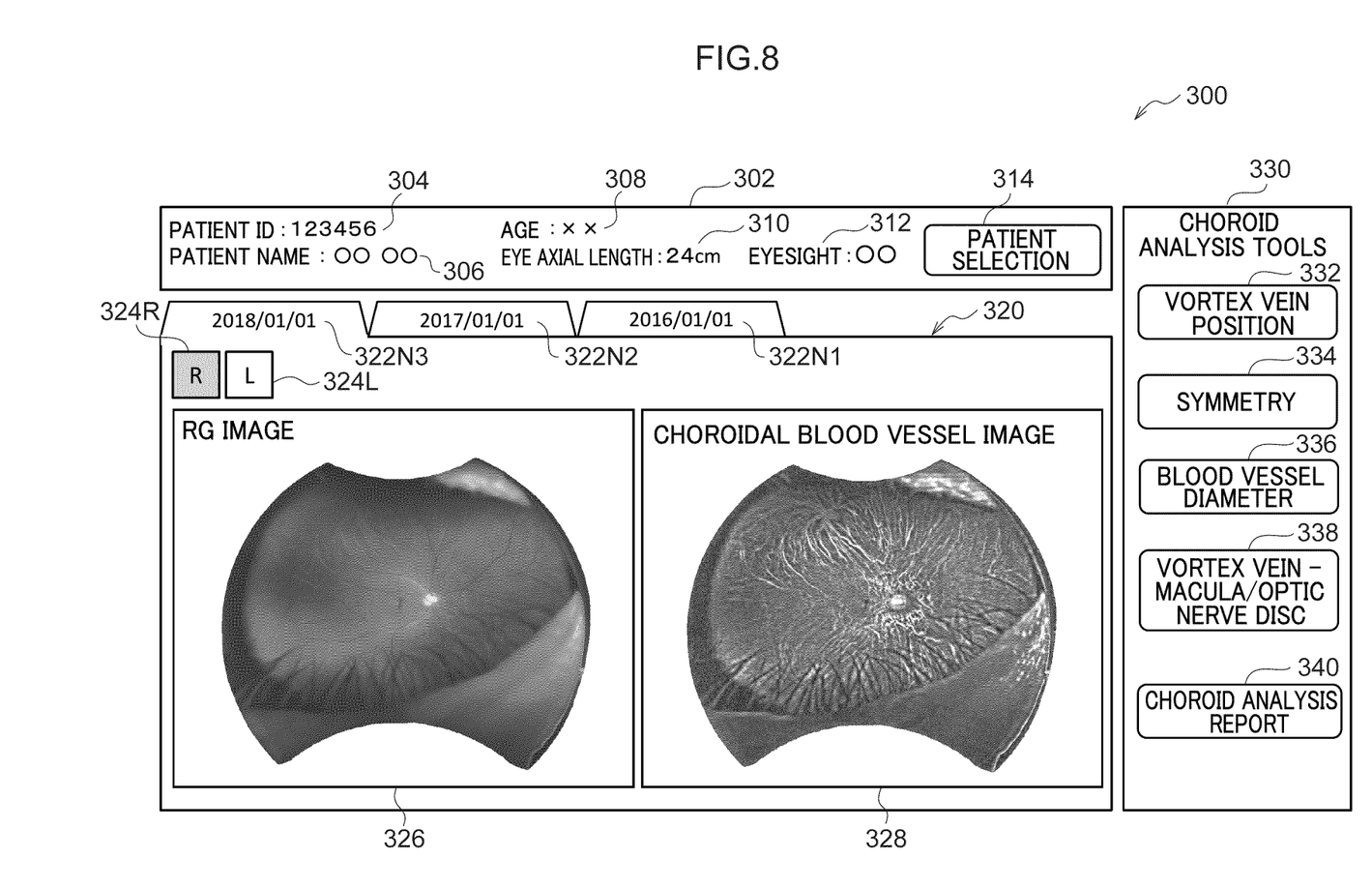
FIG. 8 is a view showing the display screen 300 of the choroidal blood vessel analysis mode when a fundus of a patient is photographed three times in a total on different days.

In comparison, if the fundus of this same patient was subsequently photographed again, for example, on Jan. 1, 2017 and Jan. 1, 2018 and the aforementioned data was acquired again each time, then as is shown in FIG. 8, an RG image and a choroid blood vessel image acquired on each of the photography dates of Jan. 1, 2016, Jan. 1, 2017, and Jan. 1, 2018 are displayed. The photography dates of Jan. 1, 2016, Jan. 1, 2017, and Jan. 1, 2018 are displayed respectively in photography date display columns 322N1, 322N2, and 322N3. For example, as is shown in FIG. 8, if a user clicks on the photography date display column 322N3 on which Jan. 1, 2018 is displayed, then the RG image and choroid blood vessel image that were obtained via photography on Jan. 1, 2018 are displayed.

As has been described above, in the present exemplary embodiment, a choroidal blood vessel image is generated.

Here, conventionally, choroid blood vessels and retinal blood vessels are present in an R image obtained when a fundus is photographed using a red-color light source, and the retinal blood vessels have an effect on the analysis when the choroidal blood vessels are being analyzed.

In contrast to this, in the present exemplary embodiment, retinal blood vessels are removed from the R image by means of image processing, so that a choroidal blood vessel image is generated that contains only choroidal blood vessels. Accordingly, it is possible to inhibit retinal blood vessels from affecting an analysis of choroidal blood vessels.

Next, various variant examples of the technology of the present disclosure will be described.

First Variant Example

In the above-described exemplary embodiment, after step 212 shown in FIG. 5, the display control unit 184 executes the processing of step 214, however, the technology of the present disclosure is not limited to this. For example, it is also possible after the processing of step 212 has ended, for the image processing program to then end, and for the display control unit 184 to execute the processing of step 214 after the management server 140 has received the command to transmit the data for a display screen for choroidal blood vessel analysis mode.

Second Variant Example

In the above-described exemplary embodiment, an example is described in which a fundus image is acquired by the ophthalmic device 110 in which an internal light irradiation angle, which is an angle from the center of the eyeball, is approximately 200 degrees. However, the technology of the present disclosure is not limited to this, and it is also possible for the technology of the present disclosure to be applied to a fundus image acquired using a fundus camera, and to a fundus image photographed using various ophthalmic devices such as, for example, an ophthalmic device or a fundus camera in which the internal irradiation angle is 100 degrees or less.

Third Variant Example

In the above-described exemplary embodiment, the management server 140 executes the image processing program, however, the technology of the present disclosure is not limited to this. It is also possible, for example, for the ophthalmic device 110 or the image viewer 150 to execute the image processing program. If the ophthalmic device 110 executes the image processing program, then the image processing program is stored in the memory 24, and the choroidal blood vessel images and choroid analysis data of step 214 are also saved to the memory 24. In contrast, if the image viewer 150 executes the image processing program, then the image processing program is stored in the memory of the image viewer 150, and the choroidal blood vessel images and choroid analysis data of step 214 are also saved to the memory of the image viewer 150.

Fourth Variant Example

In the above-described exemplary embodiment, the ophthalmic system 100 provided with the ophthalmic device 110, the eye axial length measurement device 120, the management server 140, and the image viewer 150 is described as an example, however, the technology of the present disclosure is not limited to this. It is also possible, as a first example, for the eye axial length measurement device 120 to be omitted, and for the ophthalmic device 110 to additionally perform the functions of the eye axial length measurement device 120. Furthermore, it is also possible, as a second example, for the ophthalmic device 110 to additionally perform the functions of at least one of the management server 140 and the image viewer 150. For example, if the ophthalmic device 110 also has the functions of the management server 140, then the management server 140 may be omitted. In this case, the image processing program is executed by the ophthalmic device 110 or the image viewer 150. In the same way, if the ophthalmic device 110 also has the functions of the image viewer 150, then the image viewer 150 may be omitted. As a third example, it is also possible for the management server 140 to be omitted, and for the image viewer 150 to additionally execute the functions of the management server 140.

Fifth Variant Example

In the above-described exemplary embodiment, an R fundus image photographed using R light is used as the first fundus image. However, it is also possible to use an IR fundus image photographed using IR light. In other words, because R light having a wavelength of 630~780 nm and IR light having a wavelength of more than 780 are used, the light is able to reach not only the retina, but also the choroid. IR light, in particular, enables deep regions of the choroid to be photographed. In other words, because light that enables regions of the choroid on the sclera side of the eyeball to be photographed is used, this light is able to reach the choroid from among a plurality of layers including the retina and the choroid that have different structures, and that cover the vitreous humor of the eyeball while being positioned on the outer side from the innermost side closest to the vitreous humor, and it is possible to photograph these regions reached by the light.

Sixth Variant Example

In the above-described exemplary embodiment, a fundus image is obtained by photographing the fundus of the eye being examined 12 simultaneously using G light and R light. However, the technology of the present disclosure is not limited to this. For example, it is also possible to photograph the fundus of the eye being examined 12 using G light at a different time from when the fundus of the eye being examined 12 is photographed using R light. In this case, step 208 is executed after the positions of the first fundus image (i.e., the R fundus image) and the second fundus image (i.e., the G fundus image) have been mutually aligned with each other.

Seventh Variant Example

In the above-described exemplary embodiment, a choroidal blood vessel image is generated based on the first fundus image (i.e., the R fundus image) and the second fundus image (i.e., the G fundus image). However, the technology of the present disclosure is not limited to this and it is also possible for a choroidal blood vessel image to be generated based on the first fundus image (i.e., the R fundus image). Image processing to generate a choroidal blood vessel image based on the first fundus image (i.e., the R fundus image) is shown in FIG. 9.

In the above-described exemplary embodiment, the fundus of the eye being examined 12 is photographed simultaneously using G light and R light, however, in the seventh variant example, a fundus image (i.e., an R fundus image) is obtained by photographing the fundus of the eye being examined 12 only using R light.

Figure 9:
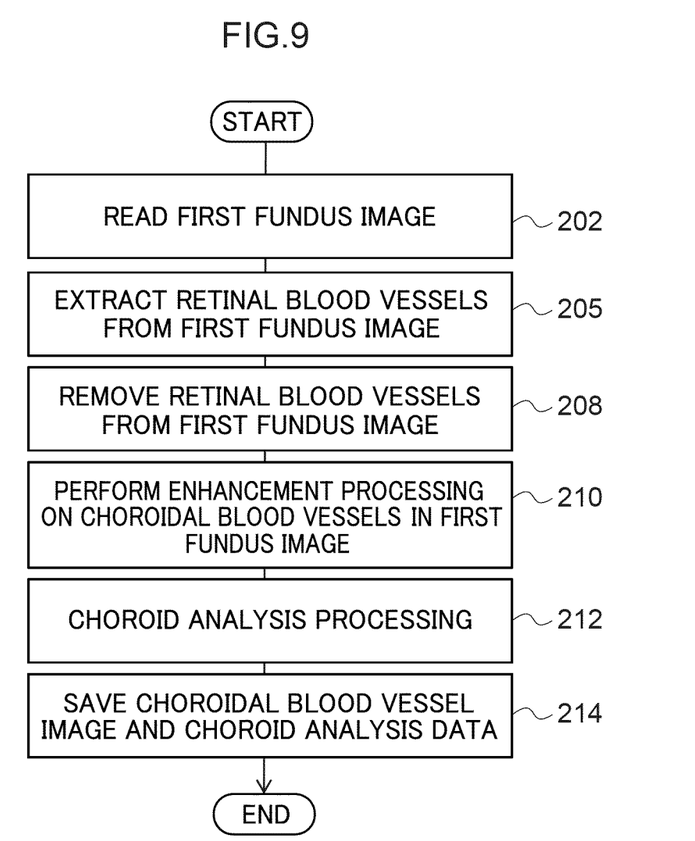
FIG. 9 is a flowchart for an image processing program of a seventh variant example.

The image processing program shown in FIG. 9 is also started when image data of a fundus image (i.e., an R fundus image) from the ophthalmic device 110 is transmitted from the ophthalmic device 110, and is received by the management server 140. Note that because the same type of processing as the image processing shown in FIG. 5 is included in the image processing shown in FIG. 9, the same descriptive symbol is allocated to processing that is the same and a detailed description thereof is omitted.

As is shown in FIG. 9, after the processing of step 202, in step 205, as a result of the image processing unit 182 performing black-hat filtering on the fundus image (i.e., the R fundus image), the retinal blood vessels are extracted from this fundus image (i.e., the R fundus image).

Note that, as is described above, information relating to blood vessels present in the retina (i.e., retinal blood vessels) and information relating to blood vessels present in the choroid (i.e., choroidal blood vessels) are contained in the fundus image (i.e., the R fundus image). However, once black-hat filtering is performed on the fundus image (i.e., the R fundus image), only information relating to the retinal blood vessels is extracted. Because the retinal blood vessels absorb not only G light, but R light as well, in the fundus image they are photographed as appearing blacker compared to peripheral areas around the blood vessels. Because of this, the retinal blood vessels can be extracted by performing black-hat filtering on the fundus image.

After step 205, steps 208 through 214 are executed.

As has been described above, in the seventh variant example, a fundus image (i.e., an R fundus image) is obtained by photographing the fundus of the eye being examined 12 using only R light, and it is possible to generate a choroidal blood vessel image from this fundus image (i.e., R fundus image).

Note that, as in the fifth variant example, the present disclosure is not limited to photographing using R light, and it is also possible to use an IR fundus image that was photographed using IR light.

Other Variant Examples

The data processing described in the foregoing exemplary embodiment is merely one example thereof. Accordingly, it should be understood that various modifications and the like such as deleting unnecessary steps, adding new steps, and rearranging the processing sequence may be made thereto insofar as they do not depart from the spirit or scope of the present disclosure.

Moreover, in the above-described embodiment, a case is illustrated in which data processing is achieved by means of a software structure which utilizes a computer, however, the technology of the present disclosure is not limited to this. For example, instead of a software structure utilizing a computer, it is also possible for the data processing to be executed solely by means of a hardware structure such as FPGA or ASIC or the like. It is also possible for a portion of the data processing to be executed by means of a software structure, and for the remaining processing to be executed by means of a hardware structure. Priority is claimed on Japanese Patent Application No. 2018-052246, filed Mar. 20, 2018, the disclosure of which is incorporated herein by reference. All references, patent applications and technical specifications cited in the present specification are incorporated by reference into the present specification to the same extent as if the individual references, patent applications and technical specifications were specifically and individually recited as being incorporated by reference.

What is claimed is:

1. An image processing method comprising:
   acquiring a fundus image including retinal blood vessels and a choroidal blood vessel by photographing a fundus using a light that passes through a retia and reaches a choroid,
   extracting the retinal blood vessels from the fundus image, and
   generating a choroidal blood vessel image by processing pixels at the positions of the retinal blood vessels in the fundus image.

2. The image processing method according to claim 1, wherein, in generating the choroidal blood vessel image, processing pixel values of the pixels at the positions of the extracted retinal blood vessels.

3. The image processing method according to claim 2, wherein the pixel values of the pixels at the positions of the retinal blood vessels are processed such that a difference between the pixel values of the pixels at the positions of the retinal blood vessels and an average pixel value of pixels surrounding the retinal blood vessels falls within a predetermined range.

4. The image processing method according to claim 1, wherein, in generating the choroidal blood vessel image, inpainting processing is performed on the positions of the extracted retinal blood vessels.

5. The image processing method according to claim 1, wherein, in extracting the retinal blood vessels, extracting the retinal blood vessels by performing black-hat filtering on the fundus image.

6. The image processing method according to claim 1, further comprising performing processing to enhance choroidal blood vessels in the choroidal blood vessel image.

7. The image processing method according to claim 1, further comprising performing processing to analyze choroidal blood vessels in the choroidal blood vessel image.

8. The image processing method according to claim 7, wherein performing the processing to analyze the choroidal blood vessels includes detecting vortex veins.

9. The image processing method according to claim 7, wherein performing the processing to analyze the choroidal blood vessels includes analyzing positions of vortex veins, macula, and/or optic nerves.

10. The image processing method according to claim 7, wherein performing the processing to analyze the choroidal blood vessels includes analyzing an orientation of a running direction of the choroidal blood vessels and/or analyzing a blood vessel diameter.

11. The image processing method according to claim 1, wherein the fundus image is photographed through a wide-angle optical system.

12. The image processing method according to claim 1, further comprising outputting image data for the choroidal blood vessel image.

13. A non-transitory computer-readable medium storing information processing program that cause the computer to
   acquiring a fundus image including retinal blood vessels and a choroidal blood vessel by photographing a fundus using a light that passes through a retia and reaches a choroid,
   extracting the retinal blood vessels from the fundus image, and
   generating a choroidal blood vessel image by processing pixels at the positions of the retinal blood vessels in the fundus image.

14. An ophthalmic device comprising:
   a photographic unit that acquires a fundus image including retinal blood vessels and a choroidal blood vessel by photographing a fundus using a light that passes through a retia and reaches a choroid;
   a processor that executes a program to perform operations comprising:
      acquiring the fundus image;
      extracting the retinal blood vessels from the fundus image, and
      generating a choroidal blood vessel image by processing pixels at the positions of the retinal blood vessels in the fundus image.

* * * * *